(12) United States Patent
Steinmueller

(10) Patent No.: US 7,293,875 B2
(45) Date of Patent: Nov. 13, 2007

(54) DEVICE FOR CARRYING OUT EXAMINATIONS OF THE HUMAN EYE

(75) Inventor: Andreas Steinmueller, Wettenberg (DE)

(73) Assignee: Oculus Optikgeraete GmbH, Wetzlar Dutenhofen (DE)

( * ) Notice: Subject to any disclaimer, the term of this patent is extended or adjusted under 35 U.S.C. 154(b) by 359 days.

(21) Appl. No.: 10/980,949

(22) Filed: Nov. 3, 2004

(65) Prior Publication Data
US 2005/0122478 A1 Jun. 9, 2005

(30) Foreign Application Priority Data
Nov. 13, 2003 (DE) .......................... 203 17 595 U

(51) Int. Cl.
*A61B 3/14* (2006.01)
(52) U.S. Cl. .................................... 351/209; 351/205
(58) Field of Classification Search ................ 351/209, 351/208, 245, 246, 205; 600/558, 489; 327/207
See application file for complete search history.

(56) References Cited

U.S. PATENT DOCUMENTS

| | | | |
|---|---|---|---|
| 4,658,214 A * | 4/1987 | Petersen | 324/207.24 |
| 4,872,460 A | 10/1989 | Nishio et al. | |
| 5,841,502 A * | 11/1998 | Miwa | 351/209 |
| 5,889,576 A * | 3/1999 | Fujieda | 351/208 |
| 6,100,681 A | 8/2000 | Tsuruta | |
| 6,573,709 B1 * | 6/2003 | Gandel et al. | 324/207.2 |
| 2002/0085173 A1 * | 7/2002 | Schippert et al. | 351/200 |
| 2003/0076477 A1 | 4/2003 | Matsumoto | |

FOREIGN PATENT DOCUMENTS

| | | |
|---|---|---|
| EP | 0 527 367 A1 | 2/1993 |
| EP | 0 850 591 A1 | 7/1998 |
| EP | 0 867 145 A2 | 9/1998 |
| EP | 0 867 145 A3 | 9/1998 |
| WO | WO99/56611 A1 | 11/1999 |

OTHER PUBLICATIONS

European Search Report for EP Counterpart Application No. EP 04019647.9-1526, 3 pgs. (Feb. 18, 2005).
German Search Report for German Counterpart Application No. 203 17 595.6, 3 pgs. (Feb. 16, 2005).

* cited by examiner

*Primary Examiner*—Hung Dang
*Assistant Examiner*—Tuyen Tra
(74) *Attorney, Agent, or Firm*—Blakely, Sokoloff, Taylor & Zafman LLP

(57) ABSTRACT

The invention relates to a device for carrying out examinations of the human eye, comprising a diagnostic unit, which when examinations are carried out is arranged in front of the left or the right eye, and comprising a frame which comprises an upper part and a lower part, wherein the lower part is arranged so as to be stationary, and wherein the upper part carries the diagnostic unit, and for positioning the diagnostic unit in front of the left or the right eye can be adjusted in the X-direction relative to the lower part, wherein the device comprises at least one sensor system with which the position of the upper part can be measured in the X-direction relative to the lower part.

18 Claims, 3 Drawing Sheets

DEVICE FOR CARRYING OUT EXAMINATIONS OF THE HUMAN EYE

FIELD

The invention relates to a device for carrying out examinations of the human eye, according to the precharacterising part of claim 1.

BACKGROUND

Generically, the device provides for a diagnostic unit, for example a keratometer or pachymeter by means of which the eye examination is carried out. For the actual examination, the diagnostic unit must be arranged in front of the eye that is being examined. To enable the treating physician to investigate either the left or the right eye of a patient, generic devices provide for a frame in which the upper part is adjustable in at least one direction relative to the lower part. This direction (X-direction) is such that the diagnostic unit which is attached to the upper part of the frame can either be arranged in front of the left or the right eye of the patient.

The known devices are associated with a disadvantage in that the allocation which shows whether the examination result refers to the left or the right eye has to be determined by the treating physician examining it and documenting it manually, for example by writing it down. This type of determination and documentation of the allocation of the examination results is not only relatively time consuming but also very susceptible to errors occurring. If the allocation of the examination results in relation to the left or the right eye is incorrectly documented, this can lead to extremely grave treatment errors. For example, treatment which is necessary on one eye might inadvertently be carried out on the other eye, namely the healthy eye.

SUMMARY OF THE INVENTION

Based on this state of the art it is thus the object of the present invention to propose a device for carrying out examinations of the human eye, with which device handling convenience for the treating physician as well as documentation safety is improved.

This object is met by a device according to the teaching of claim 1.

Advantageous embodiments of the invention form part of the subordinate claims.

The invention is based on the underlying idea of providing a sensor system on the device, which sensor system makes it possible to measure the position of the upper part in the X-direction relative to the lower part. When an examination is carried out on one eye of a patient, the measuring result of the sensor system thus makes it possible to conclude whether the examination refers to the left or to the right eye of the patient. The results of the examination can then in a very simple way be allocated to the respective measuring result of the sensor system, and can be documented if necessary so that the physician no longer has to make this allocation manually, for example by writing it down.

Devices according to the invention form part of medical technology, so that there are special requirements concerning hygiene and disinfectability. It is thus particularly advantageous if the sensor system for determining the position of the upper part relative to the lower part operates in a non-contacting manner. Non-contacting operation of the sensor system makes it possible for the various components of the sensor system to be encapsulated towards the outside, for example by arrangement in housings. Undesirable edges and crevices in which germs could lodge are avoided in this way.

Various examinations have shown that in particular magnet sensor systems are especially suited for use in devices according to the invention. These magnet sensor systems comprise at least one magnetic field sensor which interacts with at least one pick-up element which generates a magnetic field. The magnetic field sensor(s) or the pick-up element(s) is/are attached to the upper part or lower part or vice versa, so that relative movement between the upper part and the lower part results in the distance between the magnetic field sensor and the pick-up element being increased. Corresponding to the change in the distance between the magnetic field sensor and the pick-up element, the magnetic field strength which emanates from the pick-up element and which is measured by the magnetic field sensor also changes. The magnetic field strength which is measured by the magnetic field sensor can thus be evaluated to the effect that the respective distance between the upper part and the lower part can be derived from the measured value.

Magnetic field sensors which are designed in the manner of Hall probes are particularly reliable in operation. Furthermore, such Hall probes are available as standard electronic components, thus providing a significant cost advantage.

In principle the design of the pick-up element does not matter. According to a first preferred embodiment, the pick-up element is designed in the manner of a permanent magnet. Such permanent magnets provide the advantage that they do not need to be supplied with energy in order to generate the necessary magnetic field, so that installation of the permanent magnet in the device according to the invention is correspondingly simplified.

As an alternative to using permanent magnets, magnet coils can be used as pick-up elements. The magnetic field which can be generated with such magnet coils can be shaped and influenced in a very differentiated manner. Furthermore, magnetic fields with increased field strength can be generated simply and easily.

Preferably, the magnetic field sensor should be attached to the upper part, and the pick-up element to the lower part of the frame. This applies in particular if the pick-up element is designed in the manner of a permanent magnet and thus does not require its own supply of electrical energy. Supplying the magnetic field sensor with the electrical energy required poses no problem in the upper part because respective supply lines to the normal diagnostic units have to be routed through the upper part anyway.

Particularly simple signal evaluation can be achieved if the magnet sensor system comprises a left half comprising a magnetic field sensor and a pick-up element, and a right half also comprising a magnetic field sensor and a pick-up element. For position determination of the upper part relative to the lower part, the signal difference between the left half and the right half of the magnet sensor system is then measured. To this effect the magnet sensor system is preferably calibrated such that the signal difference in the middle position of the upper part is zero. In other words this means that the signal difference changes its operational sign when the middle position is traversed, and thus it is possible to derive from the operational sign of the measured signal difference whether the diagnostic unit together with the upper part was positioned in front of the left or the right eye.

In order to simplify cleaning the device, the pick-up element or the magnetic field sensor should be arranged within a housing.

In order to be able to adjust the diagnostic unit so as to be variable for different positions it is particularly advantageous if the diagnostic unit is also adjustable horizontally in the Y-direction, and is thus adjustable in a horizontal plane. Furthermore, vertical adjustment of the diagnostic unit in Z-direction can be provided, so that the diagnostic unit can then be freely positioned in space, within a specified positioning range.

Preferably, the upper part comprises a cross slide and a stand attached to the cross slide, to which stand the diagnostic unit is attached. The cross slide is adjustable in X-direction and Y-direction on a corresponding guide on the lower part. As a result, this type of design of the upper part makes it possible for various device types to be created by attaching various diagnostic units to the cross slide, wherein the sensor system according to the invention can in each application be provided unchanged.

To prevent interference with magnetic field measuring when a magnet sensor system is used, as few parts of the device as possible should be made from iron, because iron is easily magnetisable. In particular, the table for attaching the lower part of the device should be made from a nonferrous material, in particular from wood or aluminium.

In order to be able to simply document the allocation of various measuring results to the actually examined left or right eye, the device should comprise a storage unit, for example as a component of a diagnostic computer. The measured result of the sensor system, or the position data derived therefrom, can be stored in this storage unit and can be called up when required.

In principle the design of the diagnostic unit does not matter. The sensor system according to the invention is particularly suited to the use in conjunction with keratometers, pupillometers, topographers, pachymeters, cataract analysers and/or Scheimpflug cameras.

BRIEF DESCRIPTION OF THE DRAWINGS

One embodiment of the invention is diagrammatically shown in the drawings and is explained below as an example.

The following are shown.

DETAILED DESCRIPTION

Figure 1:
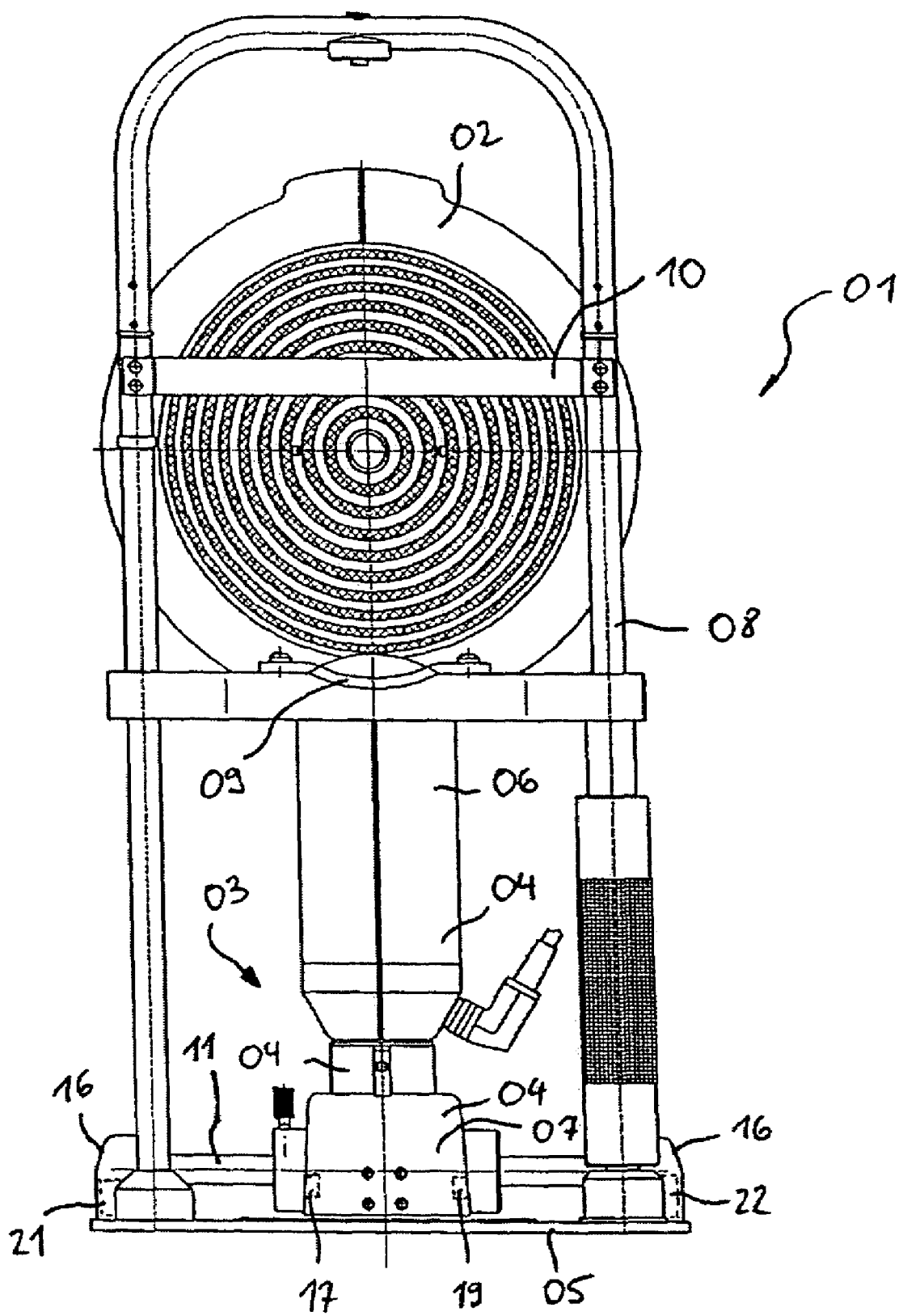
FIG. 1: a front view of a device for carrying out keratographic examinations of the human eye.
Figure 2:
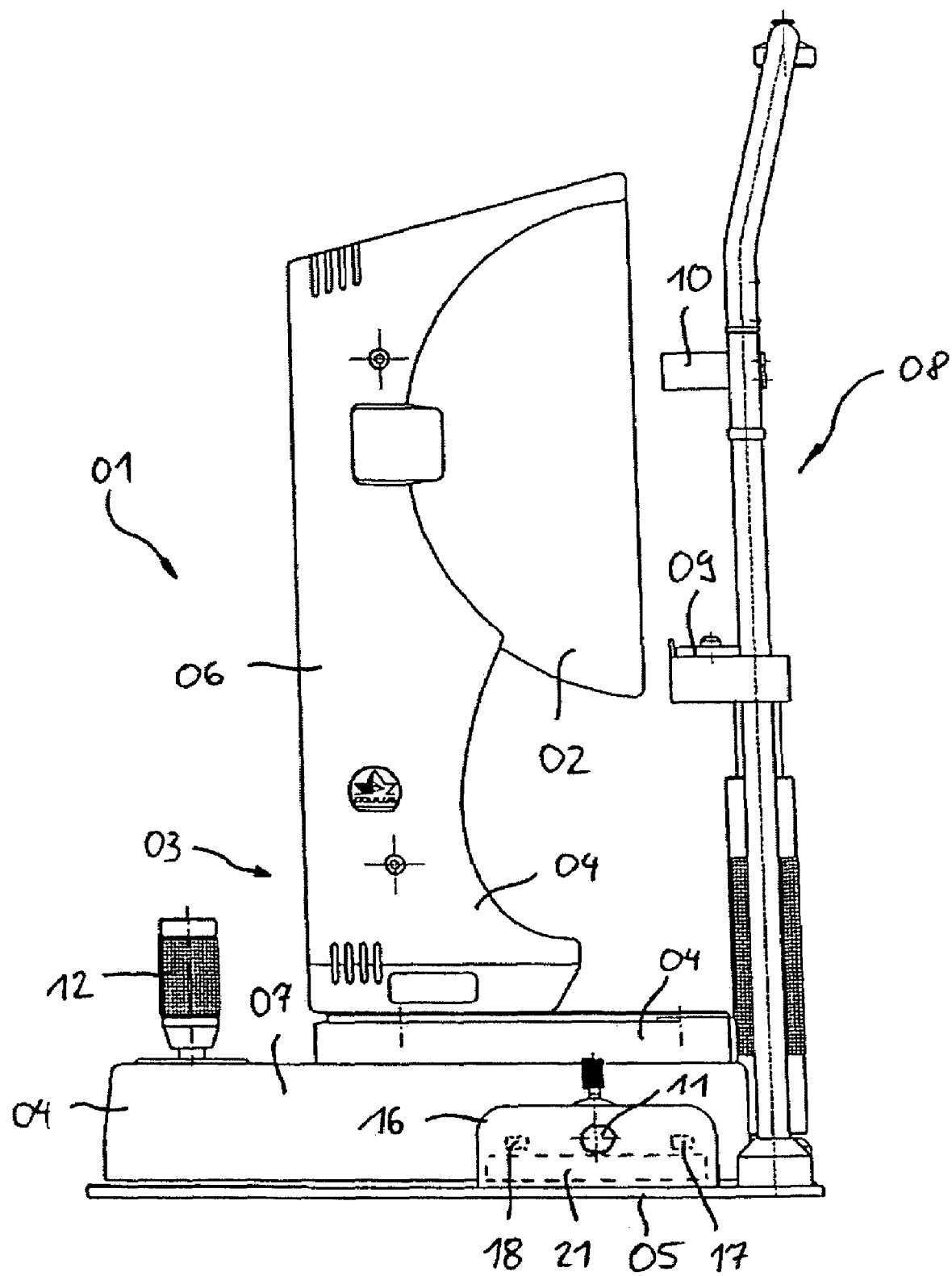
FIG. 2: a lateral view of the device according to FIG. 1.
Figure 3:
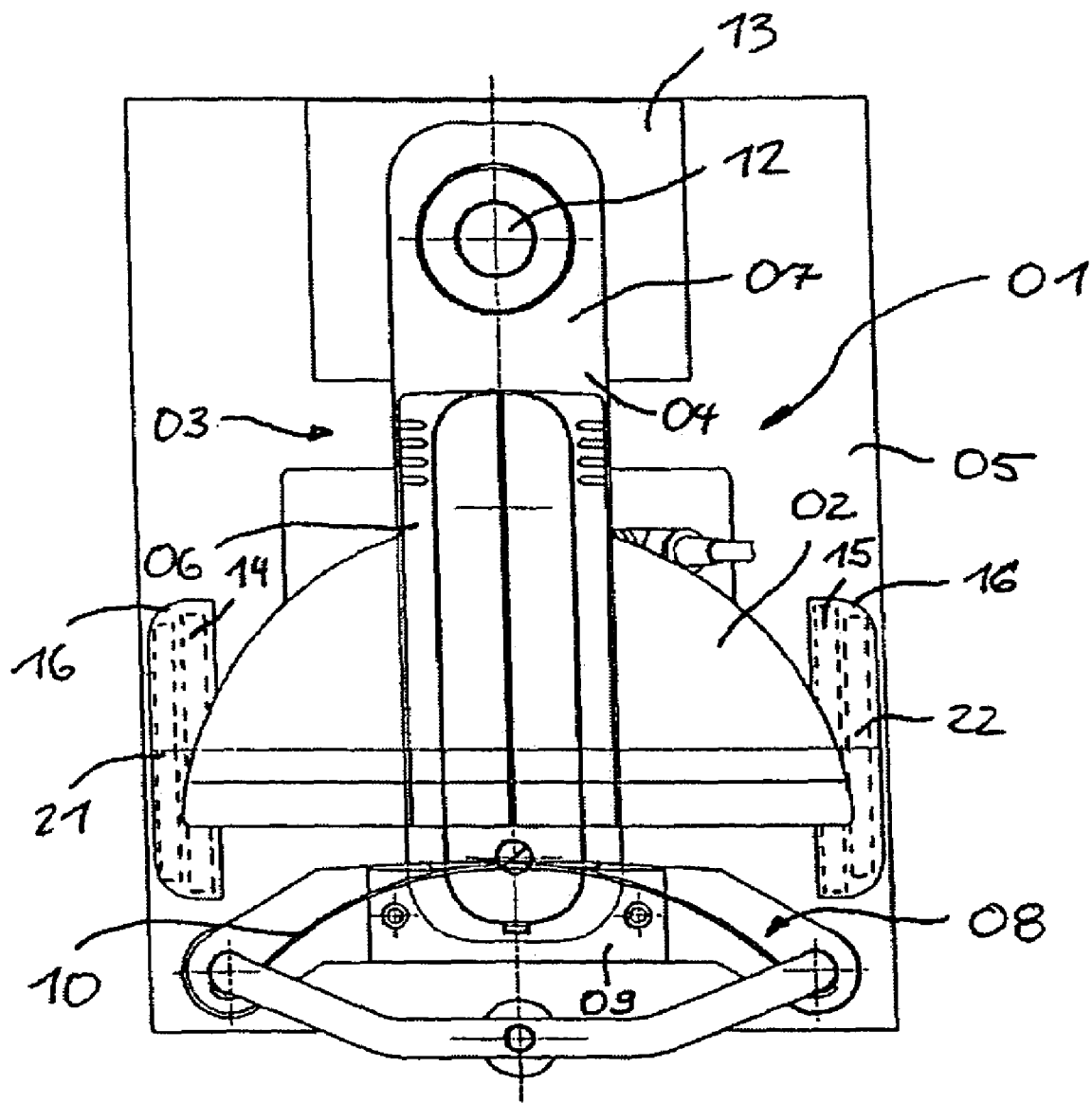
FIG. 3: a top view of the device according to FIG. 1.

FIGS. 1 to 3 show various views of a device 01 for carrying out keratographic examinations of the human eye, i.e. of a so-called keratograph. A fluorescent screen by means of which concentric circles of differing illumination intensity can be projected onto the human eye serves as a diagnostic unit 02. Using an imaging unit, for example a CD camera, placed in the centre of the diagnostic unit 02, an illumination pattern projected onto the eye can be recorded, and the characteristics of the eye can be analysed accordingly.

The diagnostic unit 02 is attached to a frame 03 which comprises a movable upper part 04 and a stationary lower part 05. The upper part 04 in turn comprises a stand 06 which carries the diagnostic unit 02, and a cross slide 07 which is adjustable in the horizontal plane in the X-direction and Y-direction. The lower part 05 and the cross slide 07 form a standard module to which various diagnostic units, for example a pachymeter or a pupillometer can be attached with the use of correspondingly adapted stands. In this way, various device types are formed, each of which comprises a sensor system according to the invention.

In front of the device 01, a support 08 is attached to the lower part 05, with said support 08 being used to fix the position of the head of the patient to be examined, with such positioning being in front of the diagnostic unit 02. The support 08 comprises a chin brace 09 onto which the chin of the patient can be placed, and a forehead brace 10 against which the forehead of the patient can be positioned. Both the height of the chin brace 09 and of the forehead brace 10 can be adjusted at the support 08, depending of the build of the patient to be examined.

For the purpose of driving the upper part 04 in the Y-direction relative to the lower part 05, a shaft 11 is provided whose longitudinal axis extends in the X-direction. The cross table 07 can be moved on this shaft 11 in the X-direction; for this purpose respective slide bushes are installed in the cross table 07. The force required for adjustment in the X-direction is provided by the operator by way of a knob 12. Below the knob 12, the cross table 07 rests on a polished steel plate 13 so that the upper part 04 is supported to the rear.

When the upper part 04 is adjusted in the Y-direction, the shaft 11 is rotationally driven. The ends of the shaft 11 comprise toothed wheels which enmesh with or engage toothed racks 14 and 15 respectively attached to the lower part 05. Towards the outside, the toothed racks 14 and 15 are covered by housings 16.

In order to determine the position of the upper part 04 in the X-direction relative to the lower part 05, the device 01 comprises a magnet sensor system which comprises four magnetic field sensors 17, 18, 19 and 20 (magnetic field sensor 20 is not shown in FIGS. 1, 2 and 3) and two pick-up elements 21 and 22 which are associated in pairs with the magnetic field sensors 17 to 20.

All the magnetic field sensors 17 to 20 are designed in the manner of Hall probes and are attached to the inside of a housing 23, on the upper part 04, so as to be invisible from the outside. Bar-shaped permanent magnets are used as pick-up elements 21 and 22, which permanent magnets are arranged in the hollow space of the housings 16 behind the toothed racks 14 and 15.

The pick-up element 21 is associated with the two magnetic field sensors 17 and 18, and together with these two magnetic field sensors constitutes the left half of the magnetic field system. The pick-up element 22 is associated with the two magnetic field sensors 19 and 20 and together with these two magnetic field sensors forms the right half of the magnet sensor system. The two magnetic field sensors 17 and 18 are used to measure the distance between the upper part 04 and the pick-up element 21, or to derive said distance from the measured results. The two magnetic field sensors 19 and 20 are used to measure the distance between the upper part 04 and the pick-up element 22, or to derive said distance from the measured results. During calibration of the magnet sensor system, the various magnetic field sensors are set such that the difference between the sensor measuring signal of the left half and of the right half of the magnet sensor system assumes the value of zero exactly in the middle position of the upper part 04. If the upper part 04 is arranged in front of the left eye of the patient, the measuring signal of the left half of the magnetic field sensor system is amplified, while the measuring signal of the right half of the magnetic field system diminishes. Accordingly, the signal difference assumes a positive operational sign. After the respective examination of the left eye has been completed, this measuring result of the magnet sensor system is stored together with the examination results so that these examination results are unequivocally allocated to the left eye of the patient. When the right eye is examined, accordingly a negative operational sign of the signal difference results, so that from the operational sign of the signal difference again the examination results can clearly be allocated to the right eye of the patient.

What is claimed is:

1. A device (01) for carrying out examinations of the human eye, comprising a diagnostic unit (02), which when examinations are carried out is arranged in front of the left or the right eye, and comprising a frame (03) which comprises an upper part (04) and a lower part (05), wherein the lower part (05) is arranged so as to be stationary, and wherein the upper part (04) carries the diagnostic unit (02) and for positioning the diagnostic unit (02) in front of the left or the right eye can be adjusted in the X-direction relative to the lower part (05) wherein the device (01) comprises at least one sensor system (17, 18, 19, 20, 21, 22) with which the position of the upper part (04) can be measured in the X-direction relative to the lower part (05), wherein the at least one sensor system is adapted to determine whether the diagnostic unit is arranged in front of the left or the right eye and wherein the sensor system (17, 18, 19, 20, 21, 22) operates in a non-contacting manner.

2. The device according to claim 1, wherein the sensor system is designed in the manner of a magnet sensor system (17, 18, 19, 20, 21, 22), wherein in the magnet sensor system (17, 18, 19, 20, 21, 22) comprises at least one magnetic field sensor (17, 18, 19, 20) interacts with at least one pick-up element (21, 22) which generates a magnetic field.

3. The device according to claim 2, wherein the magnetic field sensor (17, 18, 19, 20) is designed in the manner of a Hall probe.

4. The device according to claim 2, wherein the pick-up element (21, 22) is designed in the manner of a permanent magnet.

5. The device according to claim 4, wherein the permanent magnet (21, 22) is bar-shaped.

6. The device according to claim 2, wherein the pick-up element is designed in the manner of a magnet coil.

7. The device according to claim 2, wherein the magnetic field sensor (17, 18, 19, 20) is attached to the movably held upper part (04), and the pick-up element (21, 22) is attached to the lower part (05) which is arranged so as to be stationary.

8. The device according claim 2, wherein the magnet sensor system (17, 18, 19, 20, 21, 22) comprises a left half (17, 18, 21) in which at least one magnetic field sensor (17, 18) interacts with at least one pick-up element (21), and a right half (19, 20, 22) in which at least one magnetic field sensor (19, 20) interacts with at least one pick-up element (22).

9. The device according to claim 8, wherein for position determination of the upper part (04) relative to the lower part (05), the signal difference between the left half (17, 18, 21) and the right half (19, 20, 22) of the magnet sensor system (17, 18, 19, 20, 21, 22) is measured.

10. The device according to claim 8, wherein the pick-up element (22) of the right half (19, 20, 22) of the magnet sensor system (17, 18, 19, 20, 21, 22) and/or the pick-up element (21) of the left half (17, 18, 21) of the magnet sensor system (17, 18, 19, 20, 21, 22) is arranged laterally left or laterally right of the upper part (04) in a housing (16) on the lower part (05).

11. The device according to claim 10, wherein in the housing (16), together with the pick-up element (21, 22), in each case a toothed rack (14, 15) is arranged, which for the purpose of adjusting the upper part (04) in the Y-direction interacts with a toothed wheel on a shaft (11).

12. The device according to claim 2, wherein the magnetic field sensor (17, 18, 19, 20) of the magnet sensor system (17, 18, 19, 20, 21, 22) is arranged within a housing (23) which forms part of the upper part (04).

13. The device according to claim 1, wherein the diagnostic unit (02) is horizontally adjustable in a horizontal plane in the Y-direction.

14. The device according to claim 13, wherein the upper part (04) essentially comprises a cross slide (07) which is adjustable in the X-direction and the Y-direction, and a stand (06) which is attached to said cross slide (07), wherein the diagnostic unit (02) is attached to said stand (06).

15. The device according to claim 1, wherein the diagnostic unit is vertically adjustable in the Z-direction.

16. The device according to claim 1, wherein the lower part (05) is attached to a table made from a nonferrous material, in particular from wood or aluminium.

17. The device according to claim 1, wherein the measured result of the sensor system (17, 18, 19, 20, 21, 22) can be stored, in particular automatically, in a storage unit and can be called up from it.

18. The device according to claim 1, wherein the diagnostic unit (02) is designed in the manner of a keratometer and/or pupillometer and/or topographer and/or pachymeter and/or cataract analyser and/or a Scheimpflug camera.

* * * * *